US009847216B2

(12) United States Patent
Bailey et al.

(10) Patent No.: US 9,847,216 B2
(45) Date of Patent: Dec. 19, 2017

(54) SYSTEMS AND METHODS FOR TARGETED TOP DOWN DISCOVERY

(71) Applicant: Thermo Finnigan LLC, San Jose, CA (US)

(72) Inventors: Aaron O. Bailey, Santa Cruz, CA (US); Paul R. Gazis, Mountain View, CA (US); David M. Horn, Palo Alto, CA (US)

(73) Assignee: Thermo Finnigan LLC, San Jose, CA (US)

( * ) Notice: Subject to any disclaimer, the term of this patent is extended or adjusted under 35 U.S.C. 154(b) by 0 days.

(21) Appl. No.: 14/827,021

(22) Filed: Aug. 14, 2015

(65) Prior Publication Data

US 2017/0047209 A1    Feb. 16, 2017

(51) Int. Cl.
*H01J 49/00* (2006.01)
*G01N 30/72* (2006.01)
*G01N 30/86* (2006.01)

(52) U.S. Cl.
CPC .......... *H01J 49/0036* (2013.01); *G01N 30/72* (2013.01); *G01N 30/8679* (2013.01); *G01N 30/7233* (2013.01); *H01J 49/004* (2013.01)

(58) Field of Classification Search
CPC .... H01J 49/0036; H01J 49/004; G01N 30/72; G01N 30/7233; G01N 30/8679
See application file for complete search history.

(56) References Cited

U.S. PATENT DOCUMENTS 6,835,927 B2 * 12/2004 Becker ............... H01J 49/0036
250/281
7,606,667 B2 * 10/2009 Herold ................... G01N 30/72
250/339.07

(Continued)

FOREIGN PATENT DOCUMENTS

EP          1717586 A1    11/2006
WO      2005/113830 A2    12/2005

(Continued)

OTHER PUBLICATIONS

Bailey, et al., "Top-down 2.0: Synchronous Precursor Selection in Ion Trap Allows Co-Isolation of Multiple Intact Protein Charges on Chromatography-Timescale", 25th Conference of the Australian and New Zealand Society for Mass Spectrometry (ANZSMS) in Brisbane, Australia, Jul. 19-22, 2015, Poster.

(Continued)

*Primary Examiner* — Wyatt Stoffa
(74) *Attorney, Agent, or Firm* — David A. Schell

(57) ABSTRACT

A system for analyzing a sample includes a chromatographic device, a mass resolving device, and a data processor. The chromatographic device is configured to separate components of the sample using a chromatographic column. The mass resolving device is configured to characterize mass spectrographic properties of the separated components in an intact state, and fragment the separated components and characterize mass spectrographic properties of the resulting fragments. The data processor is configured to average chromatographic and mass spectrographic properties from a plurality of mass chromatographic data sets, generate an inclusion list identifying components for fragmentation, instruct the chromatographic device to repeat the separation of the sample and instruct the mass resolving device to fragment the components and characterize the mass spectrographic properties of the fragments, and identify at least (Continued)

one component based on the mass spectrographic properties of the intact state and the corresponding fragments.

17 Claims, 10 Drawing Sheets

(56) References Cited

U.S. PATENT DOCUMENTS

| | | | | |
|---|---|---|---|---|
| 8,030,089 | B2* | 10/2011 | Geromanos | C12Q 1/6872 436/173 |
| 8,105,838 | B2* | 1/2012 | Gorenstein | G01N 30/72 436/86 |
| 8,428,889 | B2* | 4/2013 | Wright | G01J 3/28 702/32 |
| 8,635,258 | B2* | 1/2014 | Du | G01N 30/8668 708/207 |
| 8,653,447 | B2* | 2/2014 | Mukaibatake | H01J 49/4215 250/281 |
| 8,748,809 | B2* | 6/2014 | Zabrouskov | H01J 49/0045 250/281 |
| 8,935,101 | B2 | 1/2015 | Wright | |
| 9,443,706 | B2* | 9/2016 | Gilbert | H01J 49/0031 |
| 2002/0119490 | A1* | 8/2002 | Aebersold | G01N 33/6803 435/7.1 |
| 2008/0172186 | A1* | 7/2008 | Ito | G01N 30/8624 702/23 |
| 2012/0261568 | A1 | 10/2012 | Coon et al. | |
| 2013/0116933 | A1 | 5/2013 | Geromanos et al. | |
| 2014/0252218 | A1* | 9/2014 | Wright | H01J 49/0031 250/282 |
| 2015/0340216 | A1* | 11/2015 | Kwiecien | G06K 9/00543 250/282 |

FOREIGN PATENT DOCUMENTS

| | | |
|---|---|---|
| WO | 2009/146345 A1 | 12/2009 |
| WO | 2014/096914 A1 | 6/2014 |

OTHER PUBLICATIONS

Bailey et al., "Instant spectral assignment for advanced decisiontree-driven mass spectrometry", Proceedings of the National Academy of Sciences 2012, vol. 109 (22), pp. 8411-8416.

* cited by examiner

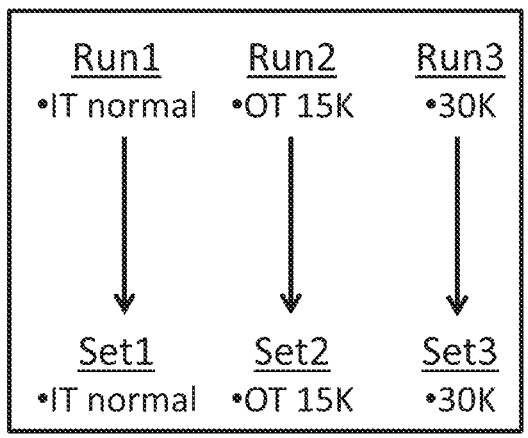
FIG 4A. Varied
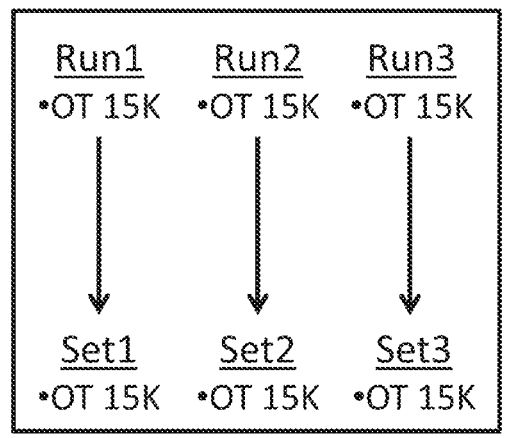
FIG 4B. Replicate
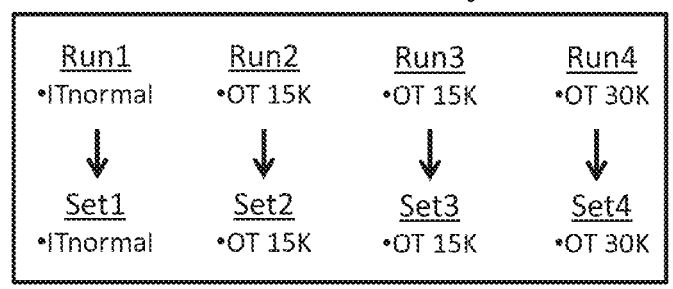
FIG 4C. Varied + Replicate

Data Output of Protein Deconvolution

| Average Mass | Sum Intensity | Number of Charge States | Number of Detected Intervals | Relative Abundance | Fractional Abundance | Scan Range | RT Range | Apex RT | Charge State | Intensity | MZ Centroid | Calculated Mass |
|---|---|---|---|---|---|---|---|---|---|---|---|---|

Harmonize Mass Data 

Generate Inclusion List and Fragmentation Parameters

Data Input to Top-down MS/MS Method

| MSX ID | Name (Average Mass) (Grouping) (Frag Params) | Start RT Range Threshold | Stop RT Range Threshold | Charge State | MZ Centroid | Frag Mode | Rxn Time/Energy | Supp Act Mode | Supp Act Rxn Energy |
|---|---|---|---|---|---|---|---|---|---|

FIG. 9

SYSTEMS AND METHODS FOR TARGETED TOP DOWN DISCOVERY

FIELD

The present disclosure generally relates to the field of chromatography and mass spectrometry including systems and methods for targeted top down discovery.

INTRODUCTION

Chromatography and Mass Spectrometry have been used to identify and quantify biological molecules, such as lipids, carbohydrates, proteins, and the like. Generally, a sample can be separated based on physical properties of the constituent molecules, such as hydrophobicity, charge, isoelectric point, and the like using liquid chromatography with the appropriate column and solvents. The eluent can be directed to a mass spectrometer, where the molecules can be detected and a mass can be determined.

Additionally, further information can be obtained for particular molecules by fragmenting the molecule and determining the mass of the individual fragments in what is known as an MS/MS experiment since the target molecule is isolated prior to fragmentation at least in part based on a mass-to-charge ratio (m/z). In various embodiments, the structure of a complex molecule can be determined based on the sizes of the resulting fragments. Targeted top down discovery can be used to target specific constituent biomolecules for detailed analysis by MS/MS.

From the foregoing it will be appreciated that a need exists for improved systems and methods for targeted top down discovery.

SUMMARY

In a first aspect, a system for analyzing a sample can include a chromatographic device configured to separate components of the sample as a function of retention time within a chromatographic column. The system can further include a mass resolving device configured to receive separated components from the chromatographic device, characterize mass spectrographic properties of a plurality of the separated components in an intact state, and fragment a plurality of the separated components and characterize mass spectrographic properties of a plurality of the resulting fragments. Additionally, the system can include a data processor configured to average chromatographic and mass spectrographic properties from a plurality of mass chromatographic data sets, generate an inclusion list identifying a plurality of components for fragmentation, instruct the chromatographic device to repeat the separation of the sample and instruct the mass resolving device to fragment the components of the inclusion list and characterize the mass spectrographic properties of the fragments, and identify at least one component based on the mass spectrographic properties of the intact state and the corresponding fragments. A mass chromatographic data set including retention time information and mass spectrographic properties at at least one resolution of the mass resolving device for a plurality of intact components from a chromatographic separation.

In various embodiments of the first aspect, the components of the sample can include biopolymers comprised of a plurality of subunits. In particular embodiments, the subunits can include sugars, amino acids, nucleotides, lipids, or any combination thereof. In particular embodiments, the biopolymers can include proteins, peptides, glycoproteins, lipoproteins, modified proteins and peptides, fragments thereof, or any combination thereof. In particular embodiments, the biopolymers can include oligosaccharides, polysaccharides, polynucleotides, oligonucleotides, phospholipids, triglycerides, phosphosphingolipids, fragments thereof, or any combination thereof.

In various embodiments of the first aspect, the plurality of mass chromatographic data sets can include first and second mass chromatographic data sets at a mass resolution of the mass resolving device. In particular embodiments, averaging chromatographic and mass spectrographic properties from a plurality of mass chromatographic data sets can include matching mass-to-charge peaks from the first and second mass chromatographic data sets based on the peaks being within a ppm range and within a retention time range; and calculating mean values for the chromatographic and mass spectrographic properties for the matched peaks.

In various embodiments of the first aspect, the plurality of mass chromatographic data sets can include a first mass chromatographic data set at a first mass resolution and a second mass chromatographic data set at a second mass resolution. In particular embodiments, averaging chromatographic and mass spectrographic properties from a plurality of mass chromatographic data sets can include matching a mass-to-charge peak from the first mass chromatographic data set to the second mass chromatographic data set is based on the mass-to-charge peak of the first mass chromatographic data set being within a ppm range and within a retention time range of the mass-to-charge peak of the second mass chromatographic data set; and recording a first portion of the chromatographic and mass spectrographic properties for the matched mass-to-charge peaks from the first mass chromatographic data set and a second portion of the chromatographic and mass spectrographic properties for the matched mass-to-charge peaks for the second mass chromatographic data set. In particular embodiments, the first mass chromatographic data set can have a lower mass resolution than the second mass chromatographic data set. In particular embodiments, the first portion of the mass spectrographic properties can include an average mass for a component calculated from mass data for a plurality of charge states, a relative abundance, an apex retention time, a start retention time, a stop retention time, or any combination thereof, and the second portion of the mass spectrographic properties can include a calculated charge state value, an intensity, a mass-to-charge centroid, a calculated mass from a mass-to-charge peak, or any combination thereof.

In various embodiments of the first aspect, the mass resolving device can include a first and second mass analyzer and the plurality of mass chromatographic data sets can include a first mass chromatographic data set at a first mass resolution from the first mass analyzer and a second mass chromatographic data set at a second mass resolution from the second mass analyzer.

In various embodiments of the first aspect, the data processor can be further configured to generate a plurality of inclusion lists at one of a plurality of mass ranges, a plurality of relative abundance ranges, or any combination thereof.

In various embodiments of the first aspect, generating the inclusion list can include selecting a charge state from a plurality of charge states of a compound based on a magnitude of a mass defect, an intensity value, or any combination thereof. In particular embodiments, multiple charge states of a component can be selected and can be fragmented substantially simultaneously.

In various embodiments of the first aspect, instructing the mass resolution device to fragment the components on the inclusion list includes providing a fragmentation mode, a fragmentation reaction energy, a fragmentation reaction time, a supplemental activation mode, a supplemental activation reaction energy, or any combination thereof for a component or a charge state of the component.

In a second aspect, a method for identifying components of a sample can include using a chromatographic device to separate components of the sample as a function of retention time within a chromatographic column, providing the separated components to a mass resolving device, using the mass resolving device to characterize chromatographic and mass spectrographic properties of a plurality of the separated components in an intact state to generate one or more mass chromatographic data sets. The mass chromatographic data set can include chromatographic and mass spectrographic properties at at least one resolution of the mass resolving device for a plurality of intact components from a chromatographic separation. The method can further include using a processor to average chromatographic and mass spectrographic properties from a plurality of mass chromatographic data sets; using the processor to generate an inclusion list identifying a plurality of components for fragmentation and parameters for fragmentation and characterization by the mass resolving device; performing additional chromatographic separations of the sample by the chromatographic device; using the mass resolving device to fragment the components of the inclusion list and characterize the mass spectrographic properties of the fragments; and identifing at least one component based on the mass spectrographic properties of the intact state and the corresponding fragments.

In various embodiments of the second aspect, the components of the sample can include biopolymers comprised of a plurality of subunits. In particular embodiments, the subunits include sugars, amino acids, nucleotides, lipids, or any combination thereof. In particular embodiments, the biopolymers can include proteins, peptides, glycoproteins, lipoproteins, modified proteins and peptides, fragments thereof, or any combination thereof. In particular embodiments, the biopolymers can include oligosaccharides, polysaccharides, polynucleotides, oligonucleotides, phospholipids, triglycerides, phosphosphingolipids, fragments thereof, or any combination thereof.

In various embodiments of the second aspect, the plurality of mass chromatographic data sets can include first and second mass chromatographic data sets at a mass resolution of the mass resolving device. In particular embodiments, averaging chromatographic and mass spectrographic properties from a plurality of mass chromatographic data sets can include matching mass-to-charge peaks from the first and second mass chromatographic data sets based on the peaks being within a ppm range and within a retention time range, and calculating mean values for the chromatographic and mass spectrographic properties for the matched peaks.

In various embodiments of the second aspect, the plurality of mass chromatographic data sets can include a first mass chromatographic data set at a first mass resolution and a second mass chromatographic data set at a second mass resolution. In particular embodiments, averaging chromatographic and mass spectrographic properties from a plurality of mass chromatographic data sets can include matching a mass-to-charge peak from the first mass chromatographic data set to the second mass chromatographic data set based on the mass-to-charge peak of the first mass chromatographic data set being within a ppm threshold and within a retention time threshold of the mass-to-charge peak of the second mass chromatographic data set; and recording a first portion of the chromatographic and mass spectrographic properties for the matched mass-to-charge peaks from the first mass chromatographic data set and a second portion of the chromatographic and mass spectrographic properties for the matched mass-to-charge peaks for the second mass chromatographic data set. In particular embodiments, the first mass chromatographic data set has a lower mass resolution than the second mass chromatographic data set. In particular embodiments, the first portion of the mass spectrographic properties can include an average mass for a component calculated from mass data for a plurality of charge states, a relative abundance, an apex retention time, a start retention time, a stop retention time, or any combination thereof, and the second portion of the mass spectrographic properties can include a calculated charge state value, an intensity, a mass-to-charge centroid, a calculated mass from a mass-to-charge peak, or any combination thereof.

In various embodiments of the second aspect, the mass resolving device can include a first and second mass analyzer and the plurality of mass chromatographic data sets can include a first mass chromatographic data set at a first mass resolution from the first mass analyzer and a second mass chromatographic data set at a second mass resolution from the second mass analyzer.

In various embodiments of the second aspect, generating an inclusion list can include generating a plurality of inclusion lists at one of a plurality of mass ranges, a plurality of relative abundance ranges, or any combination thereof.

In various embodiments of the second aspect, generating the inclusion list can include selecting a charge state from a plurality of charge states of a compound based on a magnitude of a mass defect, an intensity value, or any combination thereof. In particular embodiments, multiple charge states of a component can be selected and can be fragmented substantially simultaneously.

In various embodiments of the second aspect, the parameters for fragmentation can include a fragmentation mode, a fragmentation reaction energy, a fragmentation reaction time, a supplemental activation mode, a supplemental activation reaction energy, or any combination thereof for a component or a charge state of the component.

In a third aspect, a method for identifying components of a sample can include using a processor to average chromatographic and mass spectrographic properties from a plurality of mass chromatographic data sets for a sample. Each mass chromatographic data set can be obtained by separating components of the sample as a function of retention time on a chromatographic column of a chromatographic device and characterizing a plurality of the components in an intact state with a mass resolving device at a resolution of the mass resolving device. The method can further include using the processor to generate an inclusion list identifying a plurality of components for fragmentation, parameters for fragmentation of the components by the mass resolving device, and parameters for characterization of the fragments by the mass resolving device, performing additional chromatographic separations of the sample by the chromatographic device; using the mass resolving device to fragment the components of the inclusion list and characterize the mass spectrographic properties of the fragments; and identifying at least one component based on the mass spectrographic properties of the intact state and the corresponding fragments.

In various embodiments of the third aspect, the components of the sample can include biopolymers comprised of a plurality of subunits. In particular embodiments, the subunits can include sugars, amino acids, nucleotides, lipids, or any combination thereof. In particular embodiments, the biopolymers can include proteins, peptides, glycoproteins, lipoproteins, modified proteins and peptides, fragments thereof, or any combination thereof. In particular embodiments, the biopolymers can include oligosaccharides, polysaccharides, polynucleotides, oligonucleotides, phospholipids, triglycerides, phosphosphingolipids, fragments thereof, or any combination thereof.

In various embodiments of the third aspect, the plurality of mass chromatographic data sets can include first and second mass chromatographic data sets at a mass resolution of the mass resolving device. In particular embodiments, averaging chromatographic and mass spectrographic properties from a plurality of mass chromatographic data sets can include matching mass-to-charge peaks from the first and second mass chromatographic data sets based on the peaks being within a ppm range and within a retention time range; and calculating mean values for the chromatographic and mass spectrographic properties for the matched peaks.

In various embodiments of the third aspect, the plurality of mass chromatographic data sets includes a first mass chromatographic data set at a first mass resolution and a second mass chromatographic data set at a second mass resolution. In particular embodiments, averaging chromatographic and mass spectrographic properties from a plurality of mass chromatographic data sets can include matching a mass-to-charge peak from the first mass chromatographic data set to the second mass chromatographic data set is based on the mass-to-charge peak of the first mass chromatographic data set being within a ppm range and within a retention time range of the mass-to-charge peak of the second mass chromatographic data set; and recording a first portion of the chromatographic and mass spectrographic properties for the matched mass-to-charge peaks from the first mass chromatographic data set and a second portion of the chromatographic and mass spectrographic properties for the matched mass-to-charge peaks for the second mass chromatographic data set. In particular embodiments, the first mass chromatographic data set can have a lower mass resolution than the second mass chromatographic data set. In particular embodiments, the first portion of the mass spectrographic properties can include an average mass for a component calculated from mass data for a plurality of charge states, a relative abundance, an apex retention time, a start retention time, a stop retention time, or any combination thereof, and the second portion of the mass spectrographic properties can include a calculated charge state value, an intensity, a mass-to-charge centroid, a calculated mass from a mass-to-charge peak, or any combination thereof.

In various embodiments of the third aspect, the mass resolving device can include a first and second mass analyzer and the plurality of mass chromatographic data sets can include a first mass chromatographic data set at a first mass resolution from the first mass analyzer and a second mass chromatographic data set at a second mass resolution from the second mass analyzer.

In various embodiments of the third aspect, generating an inclusion list can include generating a plurality of inclusion lists at one of a plurality of mass ranges, a plurality of relative abundance ranges, or any combination thereof.

In various embodiments of the third aspect, generating the inclusion list can include selecting a charge state from a plurality of charge states of a compound based on a magnitude of a mass defect, an intensity value, or any combination thereof.

In particular embodiments, multiple charge states of a component can be selected and can be fragmented substantially simultaneously.

In various embodiments of the third aspect, the fragmentation parameters can include a fragmentation mode, a fragmentation reaction energy, a fragmentation reaction time, a supplemental activation mode, a supplemental activation reaction energy, or any combination thereof for a component or a charge state of the component.

DRAWINGS

For a more complete understanding of the principles disclosed herein, and the advantages thereof, reference is now made to the following descriptions taken in conjunction with the accompanying drawings, in which.

FIGS. 4A, 4B, and 4C are diagrams illustrating combinations of experiments, in accordance with various embodiments.

Figure 5:
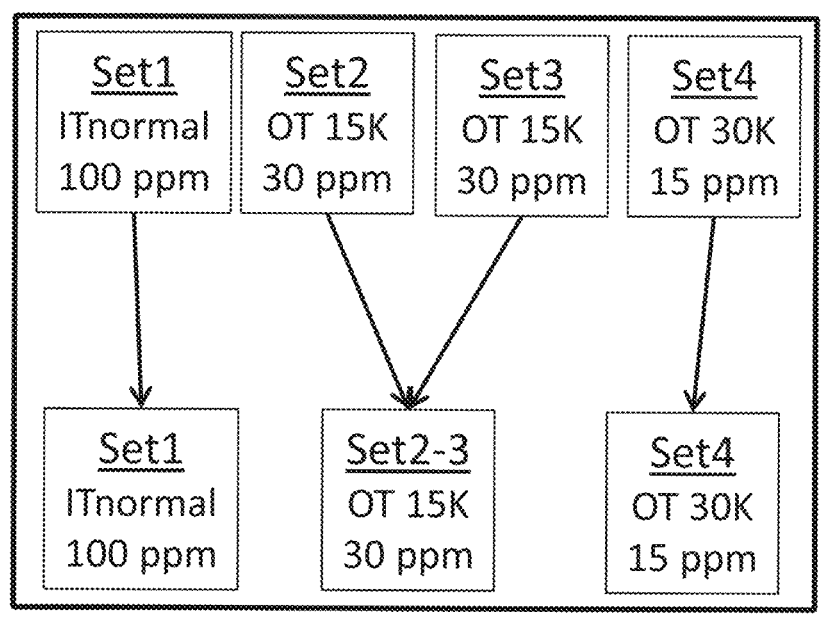
Figure 6A:
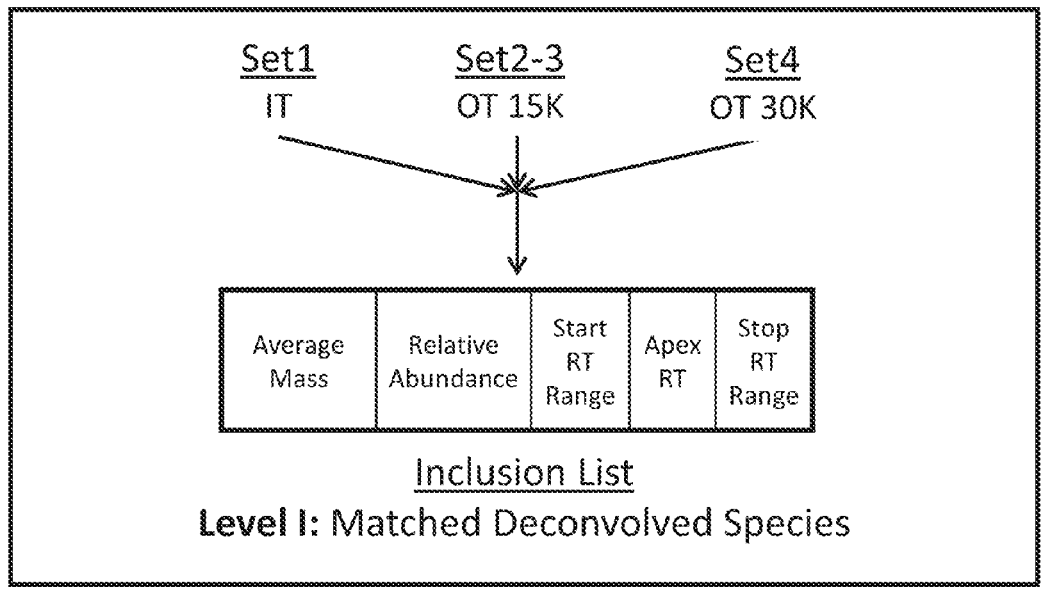
Figure 6B:
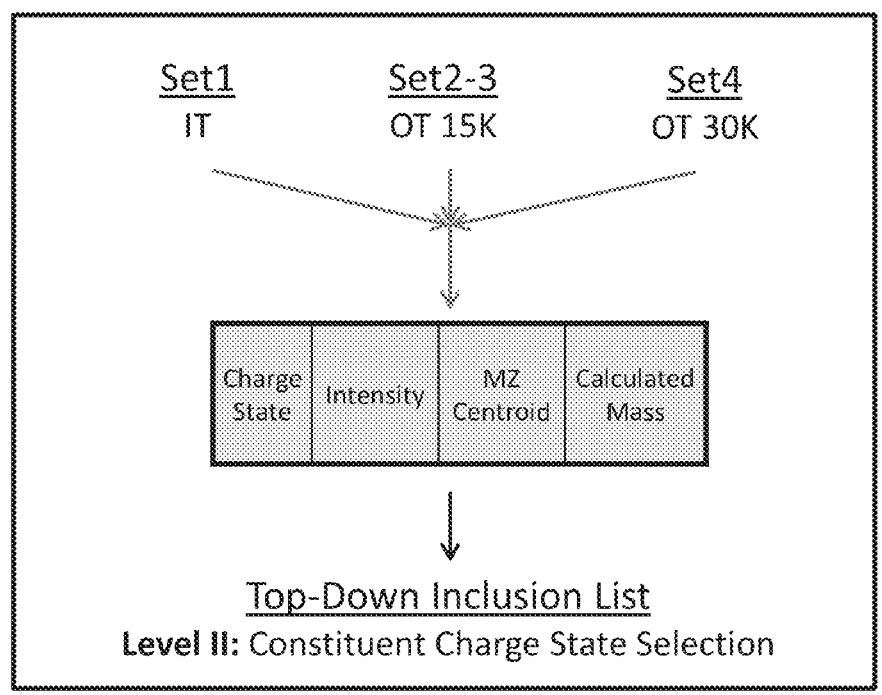

FIGS. 5, 6A, and 6B are diagrams illustrating various ways of combining data sets from multiple experiments, in accordance with various embodiments.

Figure 7:
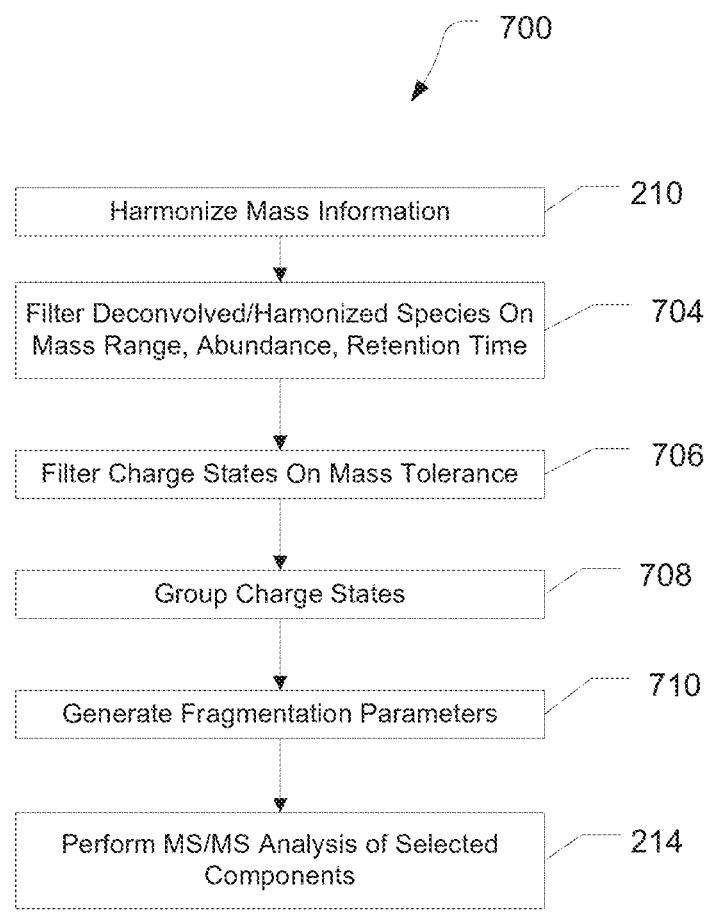

FIG. 7 is a flow diagram of an exemplary method for generating inclusion lists and fragmentation parameters, in accordance with various embodiments.

Figure 8:
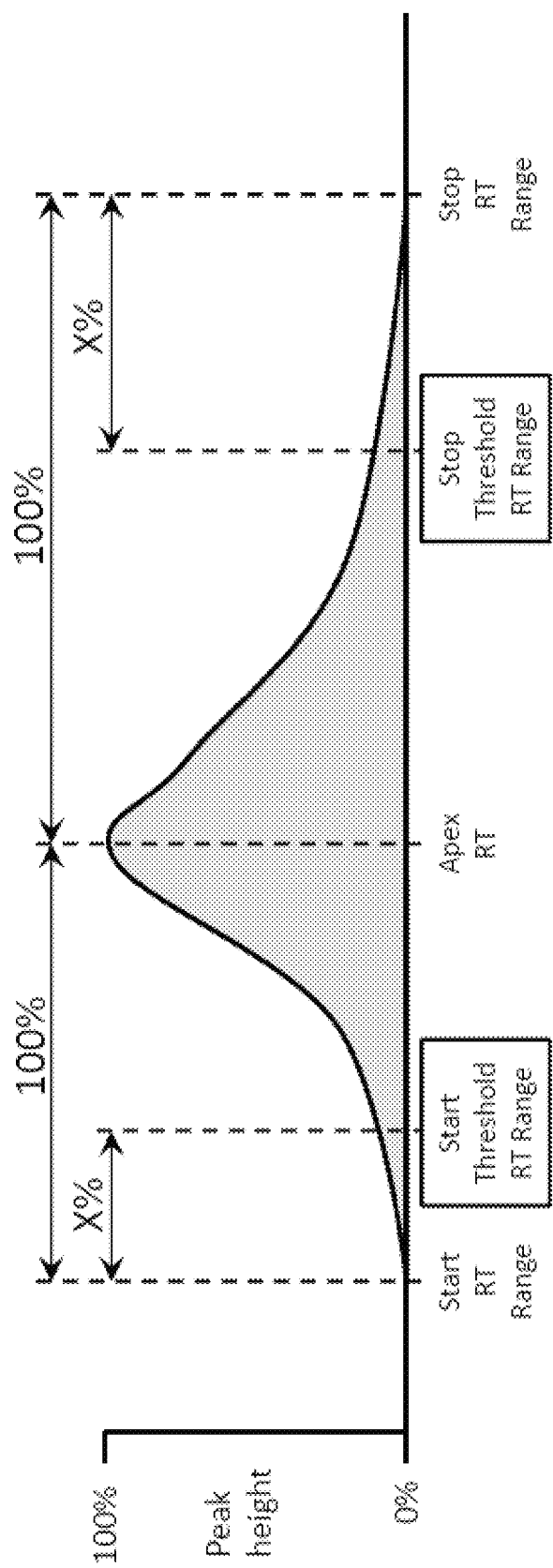

FIG. 8 is a diagram illustrating calculation of intensity thresholds, in accordance with various embodiments.

FIG. 9 is a diagram illustrating exemplary inputs and outputs, in accordance with various embodiments.

Figure 10:
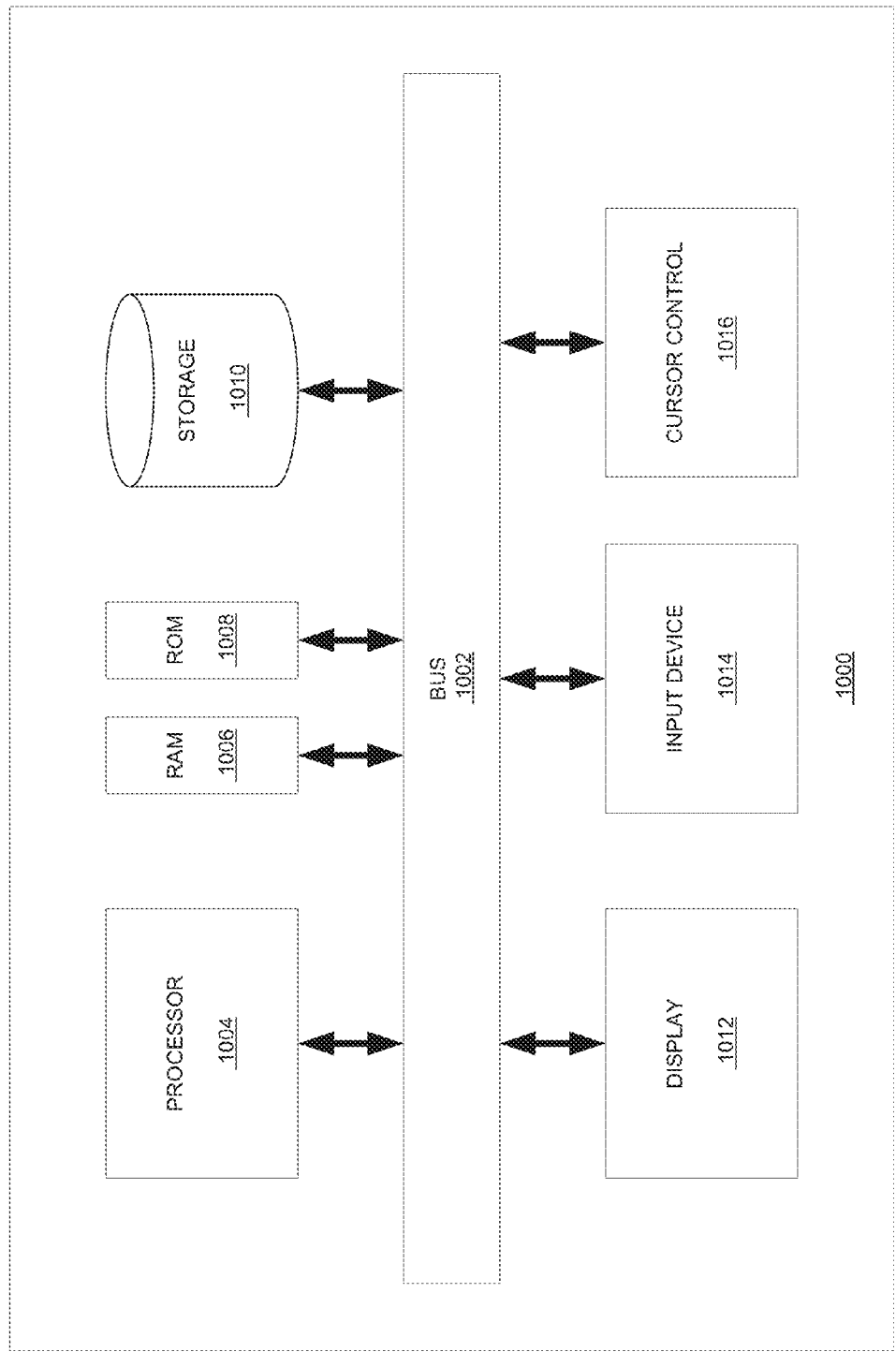

FIG. 10 is a flow block illustrating an exemplary computer system, in accordance with various embodiments.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DESCRIPTION OF VARIOUS EMBODIMENTS

Embodiments of systems and methods for targeted top down discovery are described herein.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and intern& web pages are expressly incorporated by reference in their entirety for any purpose. Unless described otherwise, all technical and scientific terms used herein have a meaning as is commonly understood by one of ordinary skill in the art to which the various embodiments described herein belongs.

It will be appreciated that there is an implied "about" prior to the temperatures, concentrations, times, pressures, flow rates, cross-sectional areas, etc. discussed in the present teachings, such that slight and insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

As used herein, "a" or "an" also may refer to "at least one" or "one or more." Also, the use of "or" is inclusive, such that the phrase "A or B" is true when "A" is true, "B" is true, or both "A" and "B" are true. Further, unless otherwise required by context, singular terms shall include pluralities and plural terms shall include the singular.

A "system" sets forth a set of components, real or abstract, comprising a whole where each component interacts with or is related to at least one other component within the whole.

Figure 1:
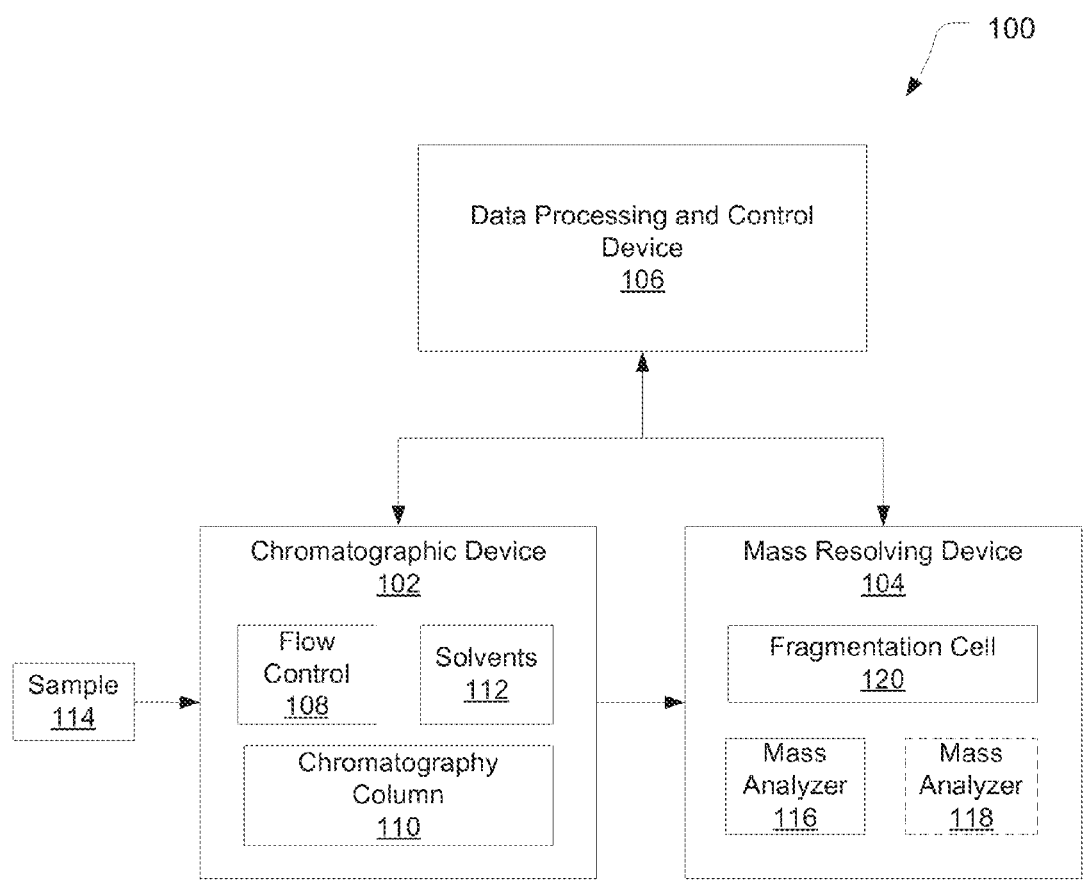
FIG. 1 is a diagram of an exemplary chromatography mass spectrometry system, in accordance with various embodiments.

FIG. 1 illustrates a typical chromatography-mass spectrometry system. Various embodiments of a chromatography and mass spectrometry system 100 can include components as displayed in the block diagram of FIG. 1. According to various embodiments, chromatography and mass spectrometry system 100 can include a chromatographic device 102, a mass resolving device 104, and a data processing and control device 106.

In various embodiments, the chromatographic device 102 can include a flow control 108 and a chromatography column 110. In various embodiments, the flow control 108 can include various pumps and valves to mix and direct a solvents 112 through the chromatography column 110. Generally, the flow control 108 can load a sample 114 on the chromatography column 110, and flow solvents 112 through the chromatography column 110. In various embodiments, the solvents can be at a constant concentration of solvent components, or the flow control 108 can blend multiple solvents 112 to form a gradient elution or stepwise elution. In various embodiments, under the control of the data processing and control device 106, the mix of solvents 112 can be quite intricate, including portions of constant concentration, portions that step from one concentration to another, and one or more portions with a gradient, even at different slopes of concentration. Generally, the chromatographic device 102 can separate components of the sample as a function of their retention time on the chromatography column 110.

In various embodiments, the mass resolving device 104 can include a mass analyzer 116, an optional second mass analyzer 118, and a fragmentation cell 120. In various embodiments, the mass analyzers 116 and 118 can separate ions based on a m/z ratio of the ions. For example, the mass analyzers 116 and 118 can include a quadrupole mass filter analyzer, a quadrupole ion trap analyzer, a time-of-flight (TOF) analyzer, an electrostatic trap (e.g., ORBITRAP) mass analyzer, Fourier transform ion cyclotron resonance (FT-ICR) mass analyzer, and the like. In various embodiments, fragmentation cell 120 can be configured to fragment the ions using collision induced dissociation (CID) electron transfer dissociation (ETD), electron capture dissociation (ECD), photo induced dissociation (PID), surface induced dissociation (SID), and the like.

Generally, the eluent from the chromatographic device 102 can be directed to a source inlet of the mass resolving device 104, where the molecules in the eluent are ionized for analysis by the mass resolving device 104. The ion source can include, but is not limited to, a matrix assisted laser desorption/ionization (MALDI) source, electrospray ionization (ESI) source, atmospheric pressure chemical ionization (APCI) source, atmospheric pressure photoionization source (APPI), inductively coupled plasma (ICP) source, electron ionization source, chemical ionization source, photoionization source, glow discharge ionization source, thermospray ionization source, and the like.

In various embodiments, the data processing and control device 106 can communicate with the chromatographic device 102 and the mass resolving device 104. For example, the data processing and control device 106 can configure the gradient profile of the chromatographic device 102 to affect separation of the sample 112. Further, the data processing and control device 106 can configure the mass resolving device 108 to determine masses for the constituent components of the sample 114, fragment selected species of ions, and analyze the mass of the resulting fragments. Additionally, the data processing and control device 106 can obtain data from both the chromatographic device 106 and the mass resolving device 104, and devise a plan for selecting and fragmenting various ionic species from the sample 114.

Figure 2:
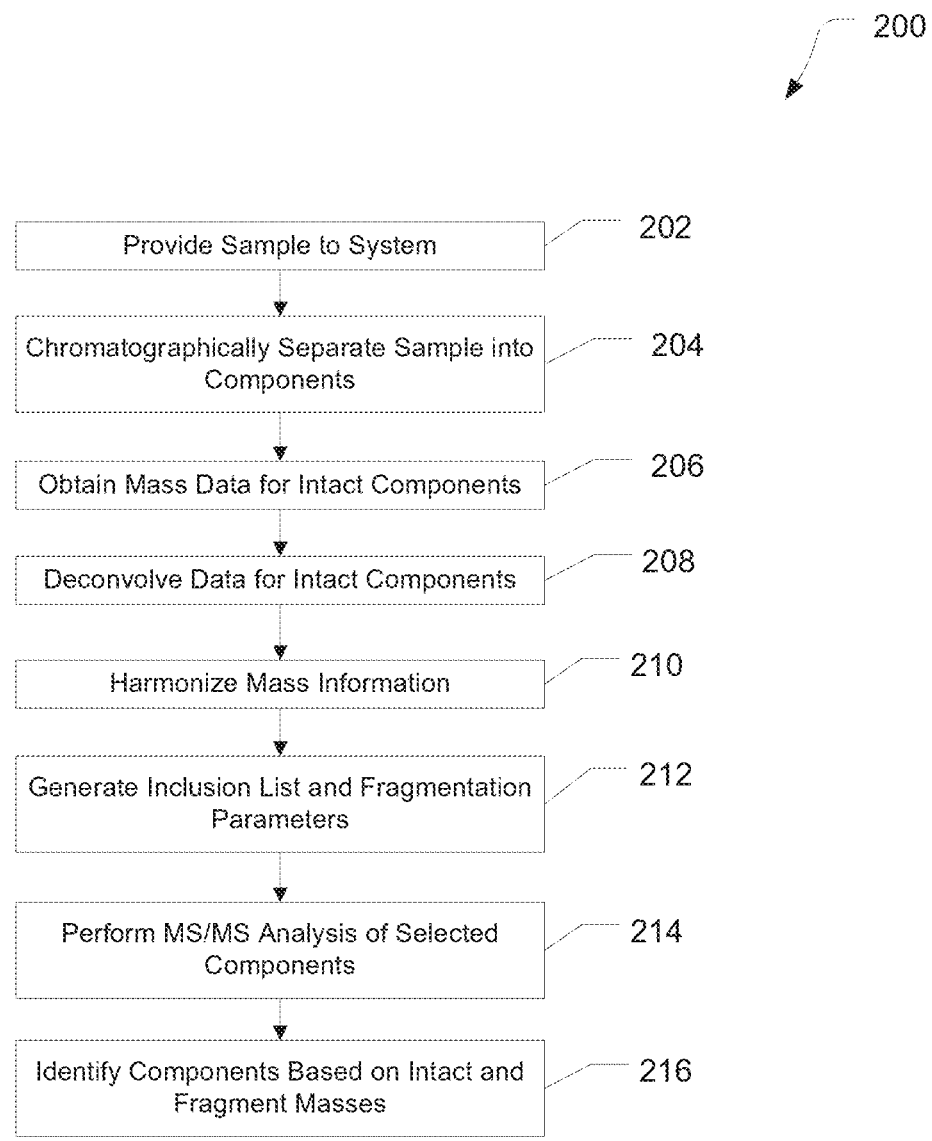
FIG. 2 is a flow diagram of an exemplary method for targeted top down discovery, in accordance with various embodiments.

FIG. 2 is a flow diagram illustrating an exemplary method 200 for analyzing components within a sample. In various embodiments, the components can include biopolymers comprised of a plurality of subunits, such as sugars, amino acids, nucleotides, lipids, or any combination thereof. In various embodiments, the biopolymers can include proteins, peptides, glycoproteins, lipoproteins, modified proteins and peptides, fragments thereof, or any combination thereof.

At 202, a sample can be provided to the system. For example, the sample may be loaded into an auto sampler such that the system can make multiple injections of the sample over time into a chromatographic device as needed. Alternatively, the sample may be manually injected into a inject port of the chromatographic device at the appropriate time.

At 204, the sample can be chromatographically separated. In various embodiments, the sample can be loaded onto a chromatography column and a solvent flow can be directed through the column to separate the components based on their interaction with a matrix within the column. For example, the matrix may include a hydrophobic species that interacts with hydrophobic molecules or hydrophobic portions of molecules. The greater the interaction between the matrix and the molecule, the slower the molecule may move through the matrix, thus separating components of the sample based on how much they interact with the matrix. In other embodiments, the matrix can include positively charged species, negatively charged species, or other species that may interact differentially with the components of the sample. In other embodiments, the matrix can include a plurality of pores, holes or different sized channels and the separation can be affected based on the size or cross section of the components, with larger components being unable to fit in certain spaces where other smaller components can fit.

At 206, a mass resolving device can obtain data for the various components of the sample in their intact state. In various embodiments, chromatography and mass spectrometry properties can be obtained at a plurality of resolutions, or using a plurality of mass analyzers of the mass resolving device. In other embodiments, chromatography and mass spectrometry properties can be obtained in replicate sets at the same resolution.

At 208, the data for the intact components can be deconvolved. In various embodiments, the data can include data for different charge states of individual components. Additionally, the presence of the components (as determined by the presence of the respective ionic species) can be correlated with the retention time from the chromatography column. In various embodiments, the deconvolved data for the intact components can be stored in a table or database of chromatography and mass spectrometry properties. Entries for a species can include an average mass, a relative abundance, a retention time range, retention time start and stop times, a retention time apex, or any combination thereof. Additionally, information about charge states for the species can include a change state, an intensity, a m/z centroid, a calculated mass, or any combination thereof.

At 210, mass information from multiple analyses can be harmonized. For example, multiple aliquots of the sample can be run through the chromatography and mass spectrometry system, generating multiple data sets. Information from the multiple data sets can be combined by matching the peaks in the mass chromatogram of one data set with corresponding peaks for the same ionic species in other data sets to create a master list.

At 212, the system can generate an inclusion list and fragmentation parameters. The inclusion list can include ions for one or more components of the sample that can be subjected to further analysis. Additionally, the fragmentation parameters can specify the method of fragmentation, as well as energy levels and times used during the fragmentation. In various embodiments, the fragmentation parameters can be specific to each ionic species.

At 214, the system can perform MS/MS analysis of the ions in the inclusions list in accordance with the fragmentation parameters. In various embodiments, the system can subject another aliquot of the sample to chromatographic separation, and the ions in the inclusion list can be isolated and subject to fragmentation and mass analysis. In various embodiments, further elucidation of the components of the sample can require multiple runs, each selecting a different subset of components for fragmentation and mass analysis.

At 216, the system can identify the components on the inclusion list based on the masses of the intact ions and the ion fragments. For example, the intact mass of a protein can be used to determine an approximate size and amino acid composition. Fragmentation of the protein can produce a protein fragment with a shorter sequence of amino acids with the composition of the protein fragment being determined by the mass. Additionally, differences in the mass of the intact protein and a protein fragment, or between two different protein fragments, can provide information about the composition of the piece that was lost from the protein fragment. While it may be necessary to fragment the protein multiple times using different fragmentation parameters, an amino acids sequence can be obtained from a series of protein fragments that differ in size by an amino acid. Similar approaches can be used to identify other biopolymers, such as carbohydrates, nucleic acids, and the like.

Figure 3:
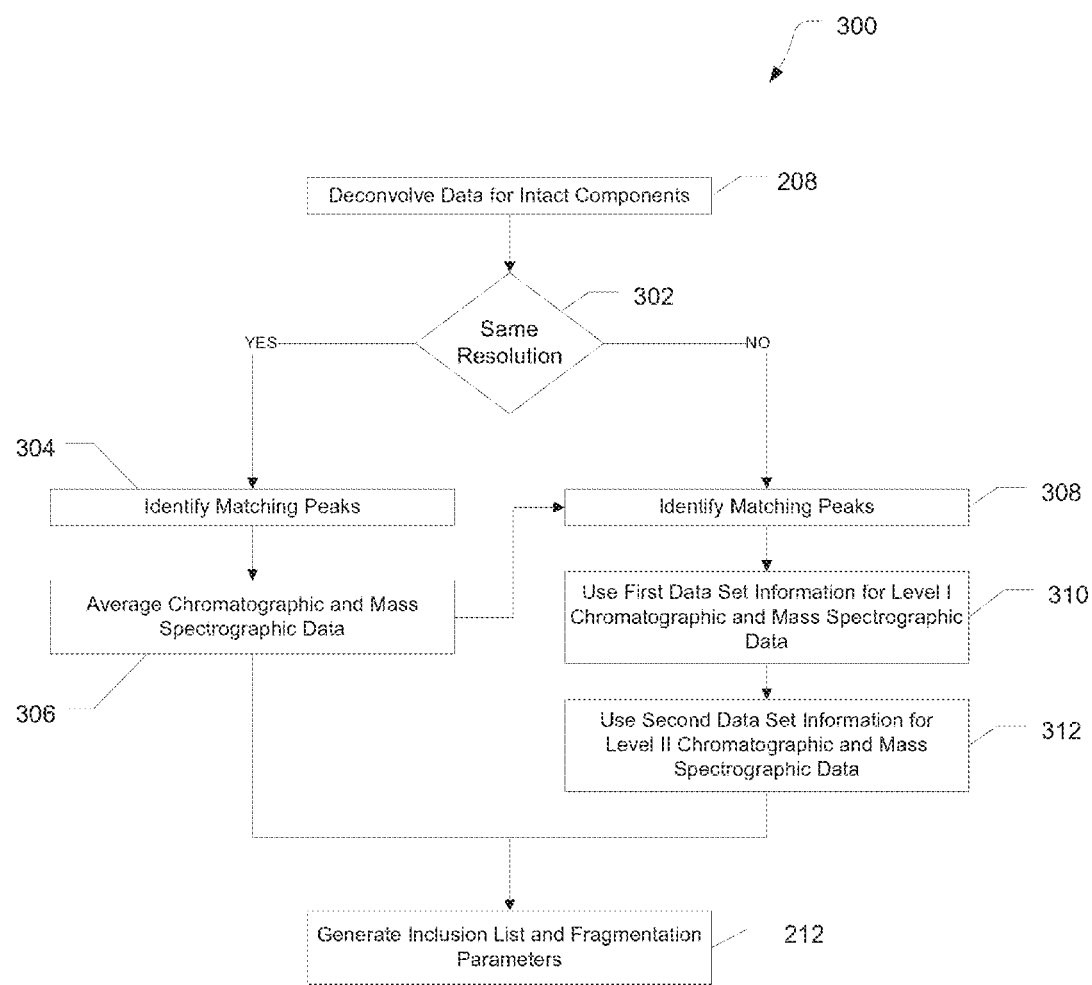
FIG. 3 is a flow diagram of an exemplary method for harmonizing mass data, in accordance with various embodiments.

FIG. 3 is a flow diagram illustrating an exemplary method 300 for harmonizing mass information. Starting at step 208 of the method shown in FIG. 2, the system can deconvolve the data obtained for the intact components to identify individual component masses, retention times, charge states, and intensities (or relative abundance).

In various embodiments, the deconvolved data can be obtained from various data sets. FIGS. 4A-4C show various combinations of data sets that can be used. FIG. 4A shows a plurality of varied data sets at differing resolution. Set 1 is a data set obtained using an ion trap mass analyzer, set 2 is a data set obtained using an ORBITRAP mass analyzer at 15K resolution, and set 3 is a data set obtained using an ORBITRAP mass analyzer at 30K resolution. FIG. 4B shows a plurality of replicate data sets at the same resolution, with each of sets 1, 2, and 3 are data sets obtained using an ORBITRAP mass analyzer at 15K resolution. FIG. 4C shows a plurality of varied and replicate data sets. Set 1 is a data set obtained using an ion trap mass analyzer, sets 2 and 3 are data sets obtained using an ORBITRAP mass analyzer at 15K resolution, and set 4 is a data set obtained using an ORBITRAP mass analyzer at 30K resolution. In various embodiments, the data sets can be obtained from one or more chromatographically separated aliquots of the sample.

Returning to FIG. 3, at 302, the system can determine if the data sets have the same resolution or varied resolutions. Generally, this can be determined based on metadata or header information for the data set.

At 304, when data sets are at the same resolution, the system can identify matching peaks, such as based on retention time and mass. In various embodiments, the peaks can be identified as matching when an m/z ratio or a calculated mass (based on the m/z ratio and identification of the charge state) is within a specified range (ppm) and the retention time is within a range, either based on the difference between a retention time apex or an overlap of the retention time ranges. At 306, the chromatographic and mass spectrometry data for the matching can be averaged across the data sets with the same resolution. For example, mean values can be calculated for an average mass, a relative abundance, a retention time range, retention time start and stop times, a retention time apex, a change state, an intensity, a m/z centroid, a calculated mass, or any combination thereof.

Returning to 302, when the data sets are not of the same resolution, the system can identify matching peaks from the data sets at various resolutions at 308. In various embodiments, the peaks can be identified as matching when an m/z ratio or a calculated mass (based on the m/z ratio and identification of the charge state) is within a specified range of a selected one of the data sets, and the retention time is within a range. In various embodiments, the selected data set can be the highest resolution data set. In other embodiments, the lowest resolution data set or another data set can be selected as the data set for comparison. In various embodiments, the specified range for the calculated mass can be larger than the specified range for matching between data sets of the same resolution to account for the different accuracy of the varied data sets.

In various embodiments, the average data from the combined data sets having the same resolution (from step 306) can be used as an input data set for combining with other data sets of various resolutions (at step 308), as illustrated in FIG. 5. In FIG. 5, Set 1 can be data obtained using an ion trap, sets 2 and 3 can be data obtained using an ORBITRAP at 15K resolution, and set 4 can be data obtained using an ORBITRAP at 30K resolution. Sets 2 and 3 can be combined, as described in steps 304 and 306 of FIG. 3, and the sets 1, 2-3, and 4 can be inputs for step 308. When set 2 and set 3 are combined, the ppm range for matching the peaks can be based on the 30 ppm error associated with the data sets. Alternatively, when sets 1, 2-3, and 4 are combined, the ppm range for matching a peak in set 2-3 with a peak in set 4 may be different from the ppm range for matching a peak in set 1 with a peak in set 4 based on the larger error associated with the set 1 data.

Returning to FIG. 3, at 310, first level chromatographic and mass spectrometry data (data related to the molecular species) can be selected to provide one data entry for the molecular species. In various embodiments, the calculated average mass, the relative abundance, the retention time range, the retention time start and stop times, the retention time apex, or any combination thereof can be taken from a first data set. The first data set can be the highest resolution data set, the lowest resolution data set, or another data set. In other embodiments, the data can be picked from various data sets, but generally the data may not be averaged across data sets with various resolutions. FIG. 6A illustrates the combination of first level chromatographic and mass spectrometry data for the matching species, with sets 1, 2-3, and 4 being combined to obtain a list of matched deconvolved species.

Returning to FIG. 3, at 312, second level mass spectrometry data (data related to a ionic species having a particular charge state) can be selected to provide one data entry for the ionic species. In various embodiments, the change state, intensity, m/z centroid, calculated mass, or any combination thereof can be taken from a second data set. The second data set can be the lowest resolution data set (as illustrated in FIG. 6B), the highest resolution data set, or another data set. In other embodiments, the data can be picked from various data sets, but generally the data may not be averaged across data sets with various resolutions. FIG. 6B illustrates the combination of second level mass spectrometry data for the matching peaks, with sets 1, 2-3, and 4 being combined to obtain a list of matched constituent charge states. When all the data sets are combined, the system can use the harmonized data set for generating the inclusion list and fragmentation parameters, at 210.

FIG. 7 shows a flow diagram illustrating an exemplary method 700 for generating inclusions lists and fragmentation parameters. Starting at step 210 of the method shown in FIG. 2, the system can harmonize the mass information, such as described in FIG. 3.

At 704, the system can filter the harmonized mass information. In various embodiments, the filtering can be performed on the mass range, relative abundance of the molecular species, the retention time, or any combination thereof. For example, if an operator is interested in higher mass proteins, the system can filter out lower mass polypeptides. Whereas if the operator is interested in lower mass polypeptides, the system can filter out molecular species with a mass above a high mass cutoff, and may also filter out molecular species with a mass below a low mass cutoff. Similarly, if the operator is interested in the most abundant biopolymers, the system can filter out any molecular species with an abundance below a cutoff, whereas if the operator is interested in biopolymers of lower abundance, the system may filter out the high abundance proteins. In various embodiments, the system may create multiple inclusion lists by stratifying the mass range or relative abundance. In this way, the system could analyze the molecular species in multiple passes, such as a high mass group, an intermediate mass group, and a low mass group. In various embodiments, the retention time filtering can be used to reduce the overall data obtained by the system, such as by eliminating molecular species that elute close to a solvent front or towards the end of an elution profile.

In various embodiments, filtering based on the retention can also include calculating a retention time intensity threshold. In various embodiments, the tails of a chromatographic peak can include insufficient molecules to obtain quality data. Additionally, the chromatographic peak may be asymmetric. It can be desirable to trim the set a retention time threshold to ignore portions of the peak with a small number of molecules. In various embodiments illustrated in FIG. 8, setting the retention time threshold based on a percentage of the retention time can limit data collection to regions with sufficient molecules. The threshold start time can be calculated by adding x % of the range between the start retention time and the apex retention time. The threshold stop time can be calculated by subtracting x % of the range between the apex retention time and the stop retention time. For asymmetric peaks, the broader side can be shortened more than the narrower side using the same percentage. In various embodiments, the percentage can be set globally, or can be calculated from a mass chromatograph.

Returning to FIG. 7 at 706, the system can filter the harmonized data on charge state. In various embodiments, charge state filtering can select charge states based on the mass defect, an intensity value, or any combination thereof.

An increased mass defect may be associated with interference of the ions in a particular charge state with ions of another molecular species. In various embodiments, a charge state of a first molecular species may be close to a charge state of second species, both in retention time and m/z. However, if both molecular species have a different mass, it may be possible for a different charge state of the first molecular species to be well resolved in m/z from any of the charge states of the second molecular species. By way of example, a molecular species of mass 600 Da may have a 2 charge ion with an m/z of 300. Another molecular species of mass 900 Da may have a 3 charge ion with an m/z of 300. However, the 600 Da molecular species would have an m/z of 200 in a 3 charge state, and the 900 Da molecular species may not have any intact ions with an m/z of 200 regardless of charge state. If the 2 molecular species have similar retention times, selecting ions with a m/z of 300 for fragmentation could results in a convoluted mixture of fragments of both molecular species, whereas selecting ions having an m/z of 200 could produce fragments of only the 600 Da molecular species.

In various embodiments, charge states with significant overlap with other species can be identified based on a mass defect calculated between the average molecular weight for the molecular species to a calculated molecular weight from the ionic species. A given molecular species can result in a plurality of ionic species with different charge states. A calculated mass can be obtained for each of the charge states by multiplying the m/z ratio times the number of charges for that ion. The average mass for the molecular species can be determined by averaging the calculated masses across all the charge states. In various embodiments, a charge state may be interfered with by another molecular species with an ion having a similar m/z value. If there is insufficient resolution to separate m/z peaks corresponding to the two ions, the peaks may merge and shift the apparent centroid of the peak.

The shift can manifest as an error in the m/z ratio, resulting in an error in the calculated mass. Ions having a larger mass defect may suffer from more interference than ions having a smaller mass tolerance, and therefore it may be desirable to isolate and fragment ions having a smaller mass tolerance.

At 708, the system can group charge states that remain in the inclusion list after filtering. In various embodiments, the system can isolate ions at multiple m/z values simultaneously, such as by using a multi-notch isolation waveform (see U.S. Patent Publication No. 2014/0339421, incorporated herein in its entirety) or via multiplexing. As such, it may be desirable to simultaneously isolate and then fragment ions corresponding to multiple charge states for a molecular species remaining in the inclusion list, rather than successively isolating and fragmenting ions from each charge state. In various embodiments, the charge states can be grouped into one set, or can be grouped into two or more sets, such as by grouping by high and low charge states, grouping by odd and even charge states, or any combination thereof.

At 710, the system can generate fragmentation parameters. In various embodiments, the fragmentation parameters may be different for each molecular species, or for each charge state (when isolated separately). Additionally, it may be desirable to fragment ions from a particular molecular species and charge state using more than one set of fragmentation parameters. For example, it may be desirable generate different fragmentation patterns, such as by using electron transfer dissociation (ETD) to form c- and z-type fragments by cleavage of the N—Cα bond, and collision induced dissociation (CID) to form b- and y-fragments by cleavage of the C—N bond. Additionally, fragmentation energies and reaction times and supplemental activation energies and reaction times can be altered to give more or less fragmentation resulting in larger or smaller fragments.

Returning to FIG. 7, at 212, the compiled inclusion list and fragmentation parameters can be used by the system to perform MS/MS analysis of the selected components of the sample, such as in step 212 in FIG. 2.

FIG. 9 provides an illustration of exemplary data from the deconvolution at step 206 of FIG. 2 and the operational parameters for the MS/MS analysis that results from generating the inclusion list and fragmentation parameters at 210 of FIG. 2, by performing the methods described in FIG. 3 and FIG. 7. The resulting inclusion list provides a start retention time threshold and a stop retention time threshold during which data collection for a molecular species can take place, and provides the charge state, m/z centroid, and fragmentation parameters for isolating and fragmenting the identified ionic species. The system can then perform substantially similar chromatographic separation of one or more aliquots of the sample and subject the resulting components to the prescribed MS/MS analysis to identify the components and sequence the biopolymers.

Computer-Implemented System

FIG. 10 is a block diagram that illustrates a computer system 1000, upon which embodiments of the present teachings may be implemented as which may incorporate or communicate with a system controller, for data processing and control device 106 shown in FIG. 1, such that the operation of components of the associated mass spectrometer may be adjusted in accordance with calculations or determinations made by computer system 1000. In various embodiments, computer system 1000 can include a bus 1002 or other communication mechanism for communicating information, and a processor 1004 coupled with bus 1002 for processing information. In various embodiments, computer system 1000 can also include a memory 1006, which can be a random access memory (RAM) or other dynamic storage device, coupled to bus 1002 for determining base calls, and instructions to be executed by processor 1004. Memory 1006 also can be used for storing temporary variables or other intermediate information during execution of instructions to be executed by processor 1004. In various embodiments, computer system 1000 can further include a read only memory (ROM) 1008 or other static storage device coupled to bus 1002 for storing static information and instructions for processor 1004. A storage device 1010, such as a magnetic disk or optical disk, can be provided and coupled to bus 1002 for storing information and instructions.

In various embodiments, processor 1004 can include a plurality of logic gates. The logic gates can include AND gates, OR gates, NOT gates, NAND gates, NOR gates, EXOR gates, EXNOR gates, or any combination thereof. An AND gate can produce a high output only if all the inputs are high. An OR gate can produce a high output if one or more of the inputs are high. A NOT gate can produce an inverted version of the input as an output, such as outputting a high value when the input is low. A NAND (NOT-AND) gate can produce an inverted AND output, such that the output will be high if any of the inputs are low. A NOR (NOT-OR) gate can produce an inverted OR output, such that the NOR gate output is low if any of the inputs are high. An EXOR (Exclusive-OR) gate can produce a high output if either, but not both, inputs are high. An EXNOR (Exclusive-NOR) gate can produce an inverted EXOR output, such that the output is low if either, but not both, inputs are high.

TABLE 1

Logic Gates Truth Table

| INPUTS | | OUTPUTS | | | | | | |
|---|---|---|---|---|---|---|---|---|
| A | B | NOT A | AND | NAND | OR | NOR | EXOR | EXNOR |
| 0 | 0 | 1 | 0 | 1 | 0 | 1 | 0 | 1 |
| 0 | 1 | 1 | 0 | 1 | 1 | 0 | 1 | 0 |
| 1 | 0 | 0 | 0 | 1 | 1 | 0 | 1 | 0 |
| 1 | 1 | 0 | 1 | 0 | 1 | 0 | 0 | 1 |

One of skill in the art would appreciate that the logic gates can be used in various combinations to perform comparisons, arithmetic operations, and the like. Further, one of skill in the art would appreciate how to sequence the use of various combinations of logic gates to perform complex processes, such as the processes described herein.

In an example, a 1-bit binary comparison can be performed using a XNOR gate since the result is high only when the two inputs are the same. A comparison of two multi-bit values can be performed by using multiple XNOR gates to compare each pair of bits, and the combining the output of the XNOR gates using and AND gates, such that the result can be true only when each pair of bits have the same value. If any pair of bits does not have the same value, the result of the corresponding XNOR gate can be low, and the output of the AND gate receiving the low input can be low.

In another example, a 1-bit adder can be implemented using a combination of AND gates and XOR gates. Specifically, the 1-bit adder can receive three inputs, the two bits to be added (A and B) and a carry bit (Cin), and two outputs, the sum (S) and a carry out bit (Cout). The Cin bit can be set to 0 for addition of two one bit values, or can be used to couple multiple 1-bit adders together to add two multi-bit values by receiving the Cout from a lower order adder. In an exemplary embodiment, S can be implemented by applying the A and B inputs to a XOR gate, and then applying the result and Cin to another XOR gate. Cout can be implemented by applying the A and B inputs to an AND gate, the result of the A-B XOR from the SUM and the Cin to another AND, and applying the input of the AND gates to a XOR gate.

TABLE 2

1-bit Adder Truth Table

| INPUTS | | | OUTPUTS | |
|---|---|---|---|---|
| A | B | Cin | S | Cout |
| 0 | 0 | 0 | 0 | 0 |
| 1 | 0 | 0 | 0 | 1 |
| 0 | 1 | 0 | 0 | 1 |
| 1 | 1 | 0 | 1 | 0 |
| 0 | 0 | 1 | 0 | 1 |
| 1 | 0 | 1 | 1 | 0 |
| 0 | 1 | 1 | 1 | 0 |
| 1 | 1 | 1 | 1 | 1 |

In various embodiments, computer system 1000 can be coupled via bus 1002 to a display 1012, such as a cathode ray tube (CRT) or liquid crystal display (LCD), for displaying information to a computer user. An input device 1014, including alphanumeric and other keys, can be coupled to bus 1002 for communicating information and command selections to processor 1004. Another type of user input device is a cursor control 1016, such as a mouse, a trackball or cursor direction keys for communicating direction information and command selections to processor 1004 and for controlling cursor movement on display 1012. This input device typically has two degrees of freedom in two axes, a first axis (i.e., x) and a second axis (i.e., y), that allows the device to specify positions in a plane.

A computer system 1000 can perform the present teachings. Consistent with certain implementations of the present teachings, results can be provided by computer system 1000 in response to processor 1004 executing one or more sequences of one or more instructions contained in memory 1006. Such instructions can be read into memory 1006 from another computer-readable medium, such as storage device 1010. Execution of the sequences of instructions contained in memory 1006 can cause processor 1004 to perform the processes described herein. In various embodiments, instructions in the memory can sequence the use of various combinations of logic gates available within the processor to perform the processes describe herein. Alternatively hardwired circuitry can be used in place of or in combination with software instructions to implement the present teachings. In various embodiments, the hard-wired circuitry can include the necessary logic gates, operated in the necessary sequence to perform the processes described herein. Thus implementations of the present teachings are not limited to any specific combination of hardware circuitry and software.

The term "computer-readable medium" as used herein refers to any media that participates in providing instructions to processor 1004 for execution. Such a medium can take many forms, including but not limited to, non-volatile media, volatile media, and transmission media. Examples of non-volatile media can include, but are not limited to, optical or magnetic disks, such as storage device 1010. Examples of volatile media can include, but are not limited to, dynamic memory, such as memory 1006. Examples of transmission media can include, but are not limited to, coaxial cables, copper wire, and fiber optics, including the wires that comprise bus 1002.

Common forms of non-transitory computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

In various embodiments, the methods of the present teachings may be implemented in a software program and applications written in conventional programming languages such as C, C++, C#, etc.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The embodiments described herein, can be practiced with other computer system configurations including hand-held devices, microprocessor systems, microprocessor-based or programmable consumer electronics, minicomputers, mainframe computers and the like. The embodiments can also be practiced in distributing computing environments where tasks are performed by remote processing devices that are linked through a network.

It should also be understood that the embodiments described herein can employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations that form part of the embodiments described herein are useful machine operations. The embodiments, described herein, also relate to a device or an apparatus for performing these operations. The systems and methods described herein can be specially constructed for the required purposes or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

Certain embodiments can also be embodied as computer readable code on a computer readable medium. The computer readable medium is any data storage device that can store data, which can thereafter be read by a computer system. Examples of the computer readable medium include hard drives, network attached storage (NAS), read-only memory, random-access memory, CD-ROMs, CD-Rs, CD-RWs, magnetic tapes, and other optical and non-optical data storage devices. The computer readable medium can also be distributed over a network coupled computer systems so that the computer readable code is stored and executed in a distributed fashion.

What is claimed is:

1. A system for analyzing a sample comprising:
   a chromatographic device configured to separate intact protein components of the sample as a function of retention time within a chromatographic column;
   a mass resolving device including a first mass analyzer and second mass analyzer, the first mass analyzer being a different type of mass analyzer than the second mass analyzer, the mass resolving device configured to:
      receive separated intact protein components from the chromatographic device;
      obtain first mass spectrographic data of a plurality of the separated intact protein components at a first resolution using the first mass analyzer and second mass spectrographic data at a second mass resolution using the second mass analyzer; and
      fragment a plurality of the separated intact protein components and characterize mass spectrographic properties of a plurality of the resulting fragments; and
   a data processor configured to:
      deconvolve the first mass spectrographic data from the first mass analyzer to obtain a first set of chromatographic and mass spectrographic properties;
      deconvolve the second mass spectrographic data from the second mass analyzer to obtain a second set of chromatographic and mass spectrographic properties;
      average the first and second chromatographic and mass spectrographic properties including retention time information and relative abundance for a matched deconvolved species;
      matching a mass-to-charge peak from the first set of chromatographic and mass spectrographic properties to the second set of chromatographic and mass spectrographic properties based on a mass-to-charge peak of the first mass chromatographic data set being within a ppm range and within a retention time range of a mass-to-charge peak of the second mass chromatographic data set;
      determining charge state, intensity, and mass-to-charge ratio for one or more constituent charge states of the matched deconvolved species based on the first and second sets of chromatographic and mass spectrographic properties;
      recording a first portion of the chromatographic and mass spectrographic properties related to a molecular species for the matched mass-to-charge peaks from the first mass chromatographic data set and a second portion of the chromatographic and mass spectrographic properties related to an ionic species having a particular charge state for the matched mass-to-charge peaks for the second mass chromatographic data set;
      generate an inclusion list identifying a plurality of components for fragmentation including at least one charge state of the matched deconvolved species;
      instruct the chromatographic device to repeat the separation of the sample and instruct the mass resolving device to fragment the components of the inclusion list and characterize the mass spectrographic properties of the fragments; and
      identify at least one component based on the mass spectrographic properties of the intact state and the corresponding fragments.

2. The system of claim 1 wherein the first mass chromatographic data set has a lower mass resolution than the second mass chromatographic data set.

3. The system of claim 1 wherein the first portion of the mass spectrographic properties includes an average mass for a component calculated from mass data for a plurality of charge states, a relative abundance, an apex retention time, a start retention time, a stop retention time, or any combination thereof, and the second portion of the mass spectrographic properties includes a calculated charge state value, an intensity, a mass-to-charge centroid, a calculated mass from a mass-to-charge peak, or any combination thereof.

4. The system of claim 1 wherein the data processor is further configured to generate a plurality of inclusion lists at one of a plurality of mass ranges, a plurality of relative abundance ranges, or any combination thereof.

5. The system of claim 1 wherein generating the inclusion list includes selecting a charge state from a plurality of charge states of a compound based on a magnitude of a mass defect, an intensity value, or any combination thereof.

6. The system of claim 5 wherein multiple charge states of a component are selected and are fragmented substantially simultaneously.

7. The system of claim 1 wherein instructing the mass resolution device to fragment the components on the inclusion list includes providing a fragmentation mode, a fragmentation reaction energy, a fragmentation reaction time, a supplemental activation mode, a supplemental activation reaction energy, or any combination thereof for a component or a charge state of the component.

8. A method for identifying components of a sample comprising:
   using a chromatographic device to separate intact biopolymer components of the sample as a function of retention time within a chromatographic column;
   providing the separated intact biopolymer components to a mass resolving device, the mass resolving device including a first mass analyzer and second mass analyzer, the first mass analyzer being a different type of mass analyzer than the second mass analyzer;
   using the mass resolving device to obtain first chromatographic and mass spectrographic data at a first resolution using the first mass analyzer and second chromatographic and mass spectrographic data at a second resolution using the second mass analyzer of a plurality of the separated biopolymer components in an intact state;

using a processor to deconvolve the first chromatographic and mass spectrographic data to obtain first chromatographic and mass spectrographic properties;

using the processor to deconvolve the second chromatographic and mass spectrographic data to obtain second chromatographic and mass spectrographic properties;

using a processor to average the first and second chromatographic and mass spectrographic properties including retention time information and relative abundance for a matched deconvolved species;

using the processor to match a mass-to-charge peak from the first set of chromatographic and mass spectrographic properties to the second set of chromatographic and mass spectrographic properties based on a mass-to-charge peak of the first mass chromatographic data set being within a ppm range and within a retention time range of a mass-to-charge peak of the second mass chromatographic data set;

using the processor to determine charge state, intensity, and mass-to-charge ratio for one or more constituent charge states of the matched deconvolved species based on the first and second chromatographic and mass spectrographic properties;

recording a first portion of the chromatographic and mass spectrographic properties related to a molecular species for the matched mass-to-charge peaks from the first mass chromatographic data set and a second portion of the chromatographic and mass spectrographic properties related to an ionic species having a particular charge state for the matched mass-to-charge peaks for the second mass chromatographic data set;

using the processor to generate an inclusion list from the recorded chromatographic and mass spectrographic properties identifying a plurality of components for fragmentation and parameters for fragmentation and characterization by the mass resolving device, the plurality of components for fragmentation including at least one charge state of the matched deconvolved species;

performing additional chromatographic separations of the sample by the chromatographic device;

using the mass resolving device to fragment the components of the inclusion list and characterize the mass spectrographic properties of the fragments; and identifying at least one component based on the mass spectrographic properties of the intact state and the corresponding fragments.

9. The method of claim 8 wherein the intact biopolymers include a plurality of subunits.

10. The method of claim 9 wherein the biopolymers include proteins, peptides, glycoproteins, lipoproteins, modified proteins and peptides, fragments thereof, or any combination thereof.

11. The method of claim 9 wherein the biopolymers include oligosaccharides, polysaccharides, polynucleotides, oligonucleotides, phospholipids, triglycerides, phosphosphingolipids, fragments thereof, or any combination thereof.

12. The method of claim 9 wherein the subunits include sugars, amino acids, nucleotides, lipids, or any combination thereof.

13. The method of claim 8 wherein the first portion of the mass spectrographic properties includes an average mass for a component calculated from mass data for a plurality of charge states, a relative abundance, an apex retention time, a start retention time, a stop retention time, or any combination thereof, and the second portion of the mass spectrographic properties includes a calculated charge state value, an intensity, a mass-to-charge centroid, a calculated mass from a mass-to-charge peak, or any combination thereof.

14. The method of claim 8 wherein generating an inclusion list includes generating a plurality of inclusion lists at one of a plurality of mass ranges, a plurality of relative abundance ranges, or any combination thereof.

15. The method of claim 8 wherein generating the inclusion list includes selecting a charge state from a plurality of charge states of a compound based on a magnitude of a mass defect, an intensity value, or any combination thereof.

16. A method for identifying components of a sample comprising:

using a processor to deconvolve first chromatographic and mass spectrographic data to obtain first chromatographic and mass spectrographic properties, the first chromatographic and mass spectrographic data obtained by separating intact protein components of the sample as a function of retention time on a chromatographic column and characterizing a plurality of the intact protein components with a first mass resolving device at a first resolution;

using the processor to deconvolve second chromatographic and mass spectrographic data to obtain second chromatographic and mass spectrographic properties characterizing the plurality of the intact protein components with a second mass resolving device at a second resolution;

using a processor to average the first and second chromatographic and mass spectrographic properties including retention time information and relative abundance for a matched deconvolved species;

using the processor to match a mass-to-charge peak from the first set of chromatographic and mass spectrographic properties to the second set of chromatographic and mass spectrographic properties based on a mass-to-charge peak of the first mass chromatographic data set being within a ppm range and within a retention time range of a mass-to-charge peak of the second mass chromatographic data set;

using the processor to determining charge state, intensity, and mass-to-charge ratio for one or more constituent charge states of the matched deconvolved species based on the first and second chromatographic and mass spectrographic properties;

recording a first portion of the chromatographic and mass spectrographic properties related to a molecular species for the matched mass-to-charge charge peaks from the first mass chromatographic data set and a second portion of the chromatographic and mass spectrographic properties related to an ionic species having a particular charge state for the matched mass-to-charge peaks for the second mass chromatographic data set;

using the processor to generate an inclusion list identifying a plurality of components for fragmentation, parameters for fragmentation of the components by the mass resolving device, and parameters for characterization of the fragments by the mass resolving device, the plurality of components for fragmentation including at least one charge state of the matched deconvolved species;

performing additional chromatographic separations of the sample by the chromatographic device;

using the mass resolving device to fragment the components of the inclusion list and characterize the mass spectrographic properties of the fragments; and identifying at least one component based on the mass spectrographic properties of the intact state and the corresponding fragments.

17. The method of claim 16 wherein the fragmentation parameters include a fragmentation mode, a fragmentation reaction energy, a fragmentation reaction time, a supplemental activation mode, a supplemental activation reaction energy, or any combination thereof for a component or a charge state of the component.

* * * * *

UNITED STATES PATENT AND TRADEMARK OFFICE
CERTIFICATE OF CORRECTION

PATENT NO. : 9,847,216 B2
APPLICATION NO. : 14/827021
DATED : December 19, 2017
INVENTOR(S) : Aaron O. Bailey et al.

Page 1 of 1

It is certified that error appears in the above-identified patent and that said Letters Patent is hereby corrected as shown below:

In the Claims

Claim 16, Column 20, Line 49:
Replace "for the matched mass-to-charge charge peaks"
With --for the matched mass-to-charge peaks--

Signed and Sealed this
Tenth Day of July, 2018

Andrei Iancu
*Director of the United States Patent and Trademark Office*